United States Patent [19]

Schrock

[11] 3,932,477

[45] Jan. 13, 1976

[54] CYCLOOCTATETRAENE COMPLEXES OF NIOBIUM AND TANTALUM

[75] Inventor: Richard Royce Schrock, Wilmington, Del.

[73] Assignee: E. I. Du Pont de Nemours and Company, Wilmington, Del.

[22] Filed: June 13, 1974

[21] Appl. No.: 478,966

[52] U.S. Cl.......................... 260/429 CY; 260/429 R
[51] Int. Cl.$^2$........................................... C07F 9/00
[58] Field of Search................ 260/429 AR, 429 CY

[56] References Cited
UNITED STATES PATENTS

| | | | |
|---|---|---|---|
| 3,450,728 | 6/1969 | Wilke et al.................. | 260/429 CY |
| 3,622,367 | 11/1971 | Haag............................ | 260/429 CY |

OTHER PUBLICATIONS

Coates, et al. Organometallic Compounds Vol. 1 p. 68 (1967).
Stone et al., Advances in Organometallic Chemistry Vol. 8 pp. 233, 269, 271 (1970).
Stone et al., Advances in Organometallic Chemistry Vol. 9, pp. 171 & 385 (1970).
Stone et al., Advances in Organometallic Chemistry Vol. 4, pp. 375 to 380 (1966).
Coates et al., Organometallic Compounds, Vol. 2, pp. 197 to 200 (1967).

*Primary Examiner*—Helen M. S. Sneed

[57] ABSTRACT

Reaction of tantalum or niobium pentachloride with dipotassium cyclooctatetraene(2-) yields $K^+M(C_8H_8)_3^-$ and $ClM(C_8H_8)_2$ (M is Ta or Nb). Likewise $BrM(C_8H_8)_2$ can be prepared from $MBr_5$. Reaction of (Cl, Br) $M(C_8H_8)_2$ with a lithium alkyl or aryl gives $RM(C_8H_8)_2$ where R is alkyl or aryl. The potassium ion of $K^+M(C_8H_8)_3^-$ can be replaced with other alkali metal ions, alkaline earth metal ions, ammonium, phosphonium, or arsonium ions by metathesis. Likewise, $(CH_3)_3TaCl_2$ and $CH_3MCl_4$ react with dipotassium cyclooctatetraene(2-) to give $(CH_3)_3Ta(C_8H_8)$ and $CH_3M(C_8H_8)_2$, respectively. The cyclooctatetraene complexes are catalysts for the oligomerization of ethylene and are useful as oxygen scavengers.

18 Claims, No Drawings

CYCLOOCTATETRAENE COMPLEXES OF NIOBIUM AND TANTALUM

BACKGROUND OF THE INVENTION

1. Field of the Invention

This invention relates to cyclooctatetraene complexes of niobium and tantalum.

2. The Prior Art

In the broad field of organo-inorganic chemistry, compounds in which hydrocarbon groups are bonded to transition-metal atoms have been important both technologically and scientifically. They have been useful, for example, as catalysts for organic reactions, petroleum additives, and sources of pure metals. Elucidation of their structures and their chemistry has provided important new scientific knowledge.

A hydrocarbon that forms complexes with transition metals of this type is 1,3,5,7-cyclooctatetraene, hereinafter referred to simply as cyclooctatetraene. Cyclooctatetraene complexes have been reported for the following transition metals, among others:

Titanium, zirconium, and hafnium, which are the Group IVB metals of the first, second, and third long periods of the Periodic Table;

Vanadium, the Group VB metal of the first long period;

Chromium, molybdenum and tungsten, the Group VIB metals of the first, second, and third long periods;

The lanthanides.

In contrast, no cyclooctatetraene complexes of niobium or tantalum have been reported. Niobium and tantalum are the Group VB elements of the second and third long periods. Thus, these two metals are surrounded in the Periodic Table by metals that do form complexes with cyclooctatetraene.

SUMMARY OF THE INVENTION

The cyclooctatetraene complexes of the present invention have the following formulae:
$Q^+M(C_8H_8)_3^-$, $RM(C_8H_8)_2$, or $(CH_3)_3Ta(C_8H_8)$,
wherein M is niobium or tantalum, R is alkyl of 1 to 8 carbons or aryl of 6 to 12 carbon atoms, Cl or Br, $Q^+$ is an equivalent of an alkali metal ion, an alkaline earth metal ion, $R'_3R''N^+$, $R''_4P^+$, or $R''_4As^+$, R' is alkyl of 1 to 8 carbons and R'' is alkyl of 1 to 8 carbons or aryl of 6 to 12 carbon atoms.

DETAILED DESCRIPTION OF THE INVENTION

The present invention is directed to novel cyclooctatetraene complexes of niobium and tantalum.

As one skilled in the art will appreciate, the cyclooctatetraene moieties bonded to niobium or tantalum, represented by $C_8H_8$ in the foregoing formulas, will not necessarily have exactly the same electronic structures as that of 1,3,5,7-cyclooctatetraene in the free, unbonded state. However, the fundamental cyclic structure involving a ring of 8 carbons, each bearing a hydrogen, is preserved. The compounds having the formula
$K^+M(C_8H_8)_3^-$
where M is tantalum or niobium can be prepared by reacting dipotassium cyclooctatetraene(2-), $K_2C_8H_8$, with the pentachloride or the pentabromide, preferably the pentachloride, of the metal M:
$3K_2C_8H_8 + MCl_5 \rightarrow KM(C_8H_8)_3 + 5KCl$ Alternatively, when M is tantalum, the product can be prepared by reacting a compound containing the hexaphenyltantalate anion with excess cyclooctatetraene, for example:
$[Li(tetrahydrofuran)_4]^+[Ta(C_6H_5)_6] + $ xs. $\rightarrow$
$C_8H_8$  $[Li(tetrahydrofuran)_4]^+[Ta(C_8H_8)_3]^-$ The cations in the above products can be replaced by other cations ($Q^+$) by conventional cation-exchange techniques. The foregoing processes are illustrated in Examples 1–6.

The quaternary ammonium, phosphonium, and arsonium entities that can be values of $Q^+$ are represented by the formulas $R'R_3''N^+$, $R'_4P^+$, and $R'_4As^+$, where R' is alkyl of 1 to 8 carbons or aryl of 6 to 12 carbons, R'' is alkyl of 1 to 8 carbons, and the R' and R'' groups can be the same or different. Examples of Q are lithium, sodium, potassium, rubidium, cesium, beryllium, magnesium, calcium, strontium, barium, tetramethylammonium, tetraisopentylammonium, heptylhexylmethylpropylammonium, triethylanilinium, trimethyl(2-naphthyl)ammonium, tetramethylphosphonium, tetrabutylphosphonium, tetra(1-naphthyl)phosphonium, trimethyl(2,4,6-trimethylphenyl)phosphonium, isobutylethylmethylisopropylphosphonium, tetramethylarsonium, tetraphenylarsonium, methyltris(p-tolyl)arsonium, and 2-biphenylyltrimethylarsonium. Preferred values of Q are the alkali metals, especially lithium, sodium, and potassium, and quaternary ammonium, phosphonium, and arsonium in which R'' is alkyl of 1–5 carbons, R' is alkyl of 1–5 carbons or phenyl, and all four groups attached to the central atom are the same.

When the above products, particularly those in which Q is an alkali metal, are made and/or purified in the presence of donor solvents such as tetrahydrofuran, acetonitrile, 1,2-dimethoxyethane ("glyme"), or 2-methoxyethyl ether ("diglyme"), one or more molecules of the solvent may be coordinated to Q. Such compounds are included in the products of the invention. The coordinated solvent molecules can usually be removed by prolonged treatment under high vacuum, sometimes at slightly elevated temperature.

Compounds of the formula
$(Cl, Br)M(C_8H_8)_2$
can be prepared by reacting a lesser amount of $K_2C_8H_8$ with $MCl_5$ or $MBr_5$; e.g.,
$2K_2C_8H_8 + MCl_5 \rightarrow ClM(C_8H_8)_2 + 4KCl$
The halogen in these compounds can be replaced by an alkyl or an aryl group by reacting with a lithium alkyl or lithium aryl compound, e.g.,
$ClM(C_8H_8)_2 + R'Li \rightarrow R'M(C_8H_8)_2 + LiCl$
Thus, this invention includes compound
$RM(C_8H_8)_2$
wherein R is Cl, Br, alkyl of 1 to 8 carbons or aryl of 6 to 12 carbon atoms.

An alkyl group is defined as a group derived from a saturated aliphatic hydrocarbon (alkane) by removal of one hydrogen atom.

An aryl group is defined as a group derived from a hydrocarbon having as its only unsaturation aromatic unsaturation in six membered ring systems, by loss of a hydrogen atom attached to a ring carbon of one such six membered ring, e.g., phenyl, naphthyl, tolyl, and the like.

Examples of hydrocarbon groups which can be R are methyl, isopropyl, t-butyl, neopentyl, hexyl, 2-ethylhexyl, phenyl, o-, m-, and p-tolyl, 3,5-dimethylphenyl, 4-hexylphenyl, 1- and 2-naphthyl, 2-ethyl-1-naphthyl, and 2-, 3-, and 4-biphenyl. Preferred values are alkyl of 1–5 carbons and phenyl.

The compounds where R is Cl or Br need not be isolated before reaction with the appropriate lithium hydrocarbyl group to make these compounds when R is a hydrocarbon group.

Alternatively, compounds of the formula

RM(C$_8$H$_8$)$_2$ where R is a hydrocarbon group can be prepared by reacting the appropriate hydrocarbylmetal tetrachloride or tetrabromide with K$_2$C$_8$H$_8$, for example:

CH$_3$MCl$_4$ + 2K$_2$C$_8$H$_8$ → CH$_3$M(C$_8$H$_8$)$_2$ + 4KCl

This method is advantageous for compounds in which R is methyl, and can be advantageous for other products when the appropriate hydrocarbylmetal tetrahalide is available.

The foregoing preparations of products containing R groups are illustrated in Examples 7–10.

Cyclooctatetraenetrimethyltantalum can be prepared by reacting trimethyltantalum dichloride with K$_2$C$_8$H$_8$:

(CH$_3$)$_3$TaCl$_2$ + K$_2$C$_8$H$_8$ → (CH$_3$)$_3$TaC$_8$H$_8$ + 2KCl

The following examples illustrate the products of the invention. To the extent possible, and except as noted, all operations were carried out in an atmosphere as free as possible from oxygen and moisture. Usually nitrogen was employed for this purpose. The molarities of solutions of potassium cyclooctatetraene(2-), K$_2$C$_8$H$_8$, were calculated from the amounts of materials used to make the solutions. Cf. Katz, J. Am. Chem. Soc. 82, 3784 (1960), and Wilke and Breil, U.S. Pat. No. 3,450,728.

EXAMPLE 1

K$^+$[Nb(C$_8$H$_8$)$_3$]$^-$

A. NbCl$_5$ (10.0 g) in 100 ml of toluene was cooled to −78°C, and 250 ml of an 0.50 M solution of K$_2$C$_8$H$_8$ in tetrahydrofuran was added dropwise with stirring over a period of 1 hour. The mixture was warmed to room temperature and allowed to stand for one day. It was filtered with the aid of diatomaceous earth and the volume of the filtrate was reduced to about 100 ml under reduced pressure. The solid that precipitated was separated by filtration and dried under reduced pressure to give 14.0 g of potassium tris(cyclooctatetraene)niobate, KNb(C$_8$H$_8$)$_3$. The nmr spectrum of the product in tetrahydrofuran-d$_8$ had a peak at 5.18 τ.

B. KNb(C$_8$H$_8$)$_3$ was prepared essentially as in Part A from 9.0 g of NbCl$_5$ and 200 ml of 0.50 M K$_2$C$_8$H$_8$, except that the potassium chloride formed as a by-product was removed by centrifugation in gas-tight bottles instead of by filtration. The potassium chloride was washed twice with 300 ml of tetrahydrofuran and again separated by centrifugation. The supernatant liquids were combined and reduced in volume to about 150 ml before filtration. The yield was 12.2 grams, after drying for about 1 hour at room temperature and about 0.1 mm. The nmr absorption spectrum in CD$_3$CN was similar to that of the product of Part A, showing a sharp peak at about 5.1 τ(C$_8$H$_8$).

| Anal. calcd. for C$_{24}$H$_{24}$KNb: | C, 64.86; | H, 5.44; | K, 8.80; | Nb, 20.90 |
|---|---|---|---|---|
| Found: | C, 64.11; | H, 5.53; | K, 8.15; | Nb, 20.68 |
| | 63.75; | 5.47; | | 21.07 |

The niobium analysis was carried out on a different, similarly prepared sample.

The corresponding sodium salt, NaNb(C$_8$H$_8$)$_3$, can be prepared by essentially the foregoing method if disodium cyclooctatetraene(2-), Na$_2$C$_8$H$_8$, is substituted for K$_2$C$_8$H$_8$. Similarly, substitution of MgC$_8$H$_8$·2.5 tetrahydrofuran (Lehmkuhl et al., J. Organometal. Chem. 46 Cl (1972)) for K$_2$C$_8$H$_8$ will give the corresponding magnesium salt, Mg[Nb(C$_8$H$_8$)$_3$]$_2$. In terms of formula (1), the latter product can be formulated as [Mg/2]$^+$[Nb(C$_8$H$_8$)$_3$]$^-$.

EXAMPLE 2

[(C$_6$H$_5$)$_4$As]$^+$[Nb(C$_8$H$_8$)$_3$]$^-$

A solution of 0.5 g of KNb(C$_8$H$_8$)$_3$ and 0.47 g of (C$_6$H$_5$)$_4$AsCl in 75 ml of warm acetonitrile was stirred for 10 minutes, during which time potassium chloride precipitated. The mixture was filtered, and the filtrate was cooled to room temperature, whereupon tetraphenylarsonium tris(cyclooctatetraene)niobate, (C$_6$H$_5$)$_4$AsNb(C$_8$H$_8$)$_3$, precipitated in purple crystals, which were separated by filtration. The yield was 0.10 g.

$^1$H nmr (CD$_2$Cl$_2$,τ): 1.9 – 2.5 (20, m, phenyl protons), 5.13 (24, s, C$_8$H$_8$).

On standing overnight at −30°C, the filtrate deposited a second crop of purple crystalline product; weight 0.12 g after filtration and drying.

| Anal. calcd. for C$_{48}$H$_{44}$AsNb: | C, 73.10; | H, 5.62 |
|---|---|---|
| Found: | C, 72.50; | H, 5.57 |

The product can advantageously be prepared in methylene chloride as solvent. After separation of potassium chloride, the solution is evaporated to dryness to isolate the salt.

[(CH$_3$)$_4$N]$^+$[Nb(C$_8$H$_8$)$_3$]$^+$ can be prepared by essentially the foregoing procedure by substituting tetramethylammonium chloride for tetraphenylarsonium chloride. If tetraethylphosphonium chloride is used, the product will be [(C$_2$H$_5$)$_4$P]$^+$[Nb(C$_8$H$_8$)$_3$]$^-$. Alkaline-earth-metal salts can also be made in this way; substitution of calcium chloride for tetraphenylarsonium chloride will give the product [Ca/2]$^+$[Nb(C$_8$H$_8$)$_3$]$^-$, i.e., Ca[Nb(C$_8$H$_8$)$_3$]$_2$. In the latter process, it may be advantageous to use tetrahydrofuran as the solvent.

EXAMPLE 3

[Li(tetrahydrofuran)$_4$]$^+$[Nb(C$_8$H$_8$)$_3$]$^-$

To a solution of 1.3 g of finely ground lithium chloride in 400 ml of tetrahydrofuran, at 50°C, was added 13.1 g of KNb(C$_8$H$_8$)$_3$, and the mixture was stirred for 1 hour while cooling to room temperature. After filtration to remove potassium chloride, the volume of the filtrate was reduced to about 200 ml under reduced pressure. Filtration and drying of the solid that precipitated gave 13 g of Li(tetrahydrofuran)$_4$Nb(C$_8$H$_8$)$_3$ as purple-black plates. A sample of the product was recrystallized from acetonitrile to give a corresponding compound in which the coordinated tetrahydrofuran had been replaced by acetonitrile. Recrystallization of the latter from tetrahydrofuran gave back the original product.

| Anal. calcd. for $C_{40}H_{56}LiNbO_4$: | C, 68.56; | H, 8.06; | Li, 0.99; | Nb, 13.26 |
|---|---|---|---|---|
| Found: | C, 67.84; | H, 7.88; | Li, 1.29; | Nb, 13.34 |
| | 67.19 | 8.04 | | 13.40 |
| | 67.58 | 8.06 | | |

$^1H$ nmr (CD$_3$CN, τ): 5.2 (24, s, C$_8$H$_8$), 6.35 (16, m, C$_4$H$_8$O), 8.22 (16, m, C$_4$H$_8$O).

EXAMPLE 4

$K^+[Ta(C_8H_8)_3]^-$

A mixture of 27.4 g of TaCl$_5$ and 100 ml toluene was cooled to −78°C, and 500 ml of an 0.46 M solution of K$_2$C$_8$H$_8$ in tetrahydrofuran was added dropwise with stirring over 2 hours. The mixture was allowed to warm to room temperature and to stand overnight. Potassium chloride that had precipitated was removed by centrifugation, washed with 500 ml of fresh tetrahydrofuran, and separated again by centrifugation. The volume of the combined supernatant liquids was reduced to about 100 ml under reduced pressure. Since no product precipitated, tetrahydrofuran was added to give a total volume of 400 ml, the solution was allowed to stand at −35°C overnight, and the solution was refluxed for 2 hours. Removal of all volatile materials under reduced pressure then gave 35 g of crude potassium tris(cyclooctatetraene)tantalate, KTa(C$_8$H$_8$)$_3$.

If rubidium cyclooctatetraene(2-), Rb$_2$C$_8$H$_8$, is substituted for K$_2$C$_8$H$_8$ in essentially the foregoing process, RbTa(C$_8$H$_8$)$_3$ will be formed.

EXAMPLE 5

$[Li(tetrahydrofuran)_4]^+[Ta(C_8H_8)_3]^-$

[Li(tetrahydrofuran)$_4$]$^+$[Ta(C$_6$H$_5$)$_6$]$^-$ was prepared from TaCl$_5$, C$_6$H$_5$Li, and tetrahydrofuran as described in assignee's co-pending application Ser. No. 191,902, filed Oct. 22, 1971, in the name of Frederick N. Tebbe (Tebbe CR-7259).

A mixture of 2.0 g of this compound, 3.0 g of cyclooctatetraene, and 50 ml of tetrahydrofuran was refluxed for one day in the absence of light. The solution was filtered, and its volume was reduced to about 10 ml. After standing at −30°C for 1 hour, it had deposited red-black crystals of Li(C$_4$H$_8$O)$_4$Ta(C$_8$H$_8$)$_3$, which were separated and dried; yield 0.200 g.

| Anal. calcd. for $C_{40}H_{56}LiO_4Ta$: | C, 60.91; | H, 7.16; | Li, 0.88 |
|---|---|---|---|
| Found: | C, 60.49; | H, 7.01; | Li, 1.01 |
| | 60.92 | 7.08 | |

The $^1H$ nmr absorption spectrum was essentially identical with that of the corresponding niobium compound (Example 3).

On addition of ethyl ether (10 ml) to the filtrate, followed by standing for 3 days at −33°C, an additional 0.180 g of product was obtained.

The foregoing process is the preferred method for making Li(C$_4$H$_8$O)$_4$Ta(C$_8$H$_8$)$_3$. The product can also be made by reacting TaCl$_5$ with K$_2$C$_8$H$_8$, as in Example 4, and then reacting the intermediate KTa(C$_8$H$_8$)$_3$, without isolation, with LiCl, both steps being carried out in the presence of tetrahydrofuran.

EXAMPLE 6

$[(C_6H_5)_4As]^+[Ta(C_8H_8)_3]^-$

Li(tetrahydrofuran)$_4$Ta(C$_8$H$_8$)$_3$ (0.090 g) was mixed with 10 ml of ethyl alcohol, and a solution of 0.060 g of tetraphenylarsonium chloride in 10 ml of ethyl alcohol was immediately added. Fine red crystals precipitated and were separated by filtration. They were dissolved in about 5 ml of methylene chloride. Dropwise addition of ethyl ether to this solution caused tetraphenylarsonium tris(cyclooctatetraene)tantalate, (C$_6$H$_5$)$_4$As-Ta(C$_8$H$_8$)$_3$, to crystallize in deep-red plates, which were separated by filtration and dried; yield 0.080 g. The $^1H$ nmr absorption spectrum of the product was identical with that of the corresponding niobium compound (Example 2).

If triethylanilinium chloride is substituted for tetraphenylarsonium chloride in essentially the foregoing process, the product will be [(C$_2$H$_5$)$_3$(C$_6$H$_5$)N]$^+$[Ta(C$_8$H$_8$)$_3$]$^-$. If diisobutyldiphenylphosphonium bromide is used, the product will be [(i-C$_4$H$_9$)$_2$(C$_6$H$_5$)$_2$P]$^+$[Ta(C$_8$H$_8$)$_3$]$^-$.

EXAMPLE 7

$C_6H_5Nb(C_8H_8)_2$

A. A mixture of 10.0 g of NbCl$_5$ and 200 ml of toluene was cooled to −78°C, and 165 ml of an 0.45 M solution of K$_2$C$_8$H$_8$ in tetrahydrofuran was added dropwise with stirring over 30 minutes. To the resulting mixture, which contained ClNb(C$_8$H$_8$)$_2$, was added 20 ml of a 2 M solution of C$_6$H$_5$Li in benzene/ethyl ether (77/23). The mixture was warmed to room temperature and centrifuged to remove potassium chloride, following which the supernatant liquid was reduced in volume to about 250 ml and allowed to stand for 1 day. The brown crystalline solid that was deposited was separated by filtration and dried, to give 3.9 g of bis(cyclooctatetraene)phenylniobium, C$_6$H$_5$Nb(C$_8$H$_8$)$_2$. A second crop, 2.5 g, was obtained by reducing the volume of the filtrate to about 100 ml and allowing it to stand at −30°C overnight, followed by filtration and drying. Part of the latter product (1.0 g) was recrystallized by dissolving it in 15 ml of methylene chloride, diluting the solution with hexane, and allowing the mixture to stand overnight at −30°C; recovery 0.5 g.

$^1H$ nmr (CD$_2$Cl$_2$, τ, 0°C): 2.56 (2, dd, J = 7.5, 1.5, ortho protons), 3.09 (3, m, meta and para protons), 4.10 (8, s, C$_8$H$_8$), 4.57 (8, s, C$_8$H$_8$). The halfheight width of the C$_8$H$_8$ peaks is approximately 1 Hz at 0°C and 3 Hz and 35°C. Pronounced broadening of these resonances occurs at higher temperatures along with apparent decomposition.

B. A larger amount of C$_6$H$_5$Nb(C$_8$H$_8$)$_2$ was made by essentially the method of Part A from 50 g of NbCl$_5$, 600 ml of toluene, 800 ml of 0.46 M K$_2$C$_8$H$_8$ in tetrahydrofuran, and 98 ml of 17.82% C$_6$H$_5$Li in benzene/ether. The combined solids (two crops) obtained by reduction of the volume of the supernatant liquid following centrifugation were washed with acetonitrile, washed with ethyl ether, and extracted with methylene chloride. Reduction of the volume of the extract gave C$_6$H$_5$Nb(C$_8$H$_8$)$_2$ in two crops; total yield 27 g. For recrystallization, the product, together with 8 g of the compound from another run, was dissolved in 700 ml of tetrahydrofuran at 60°C. The solution was filtered, and the volume of the filtrate was reduced to 400 ml under reduced pressure. Red-brown plates of $C_6H_5Nb(C_8H_8)_2$ precipitated and were separated by filtration and dried.

| Anal. calcd. for | | | |
|---|---|---|---|
| $C_{22}H_{21}Nb$: | C, 69.85; | H, 5.60; | Nb, 24.56 |
| Found: | C, 68.37; | H, 5.89; | Nb, 23.65 |
| | 68.52 | 5.71 | 23.77 |

The intermediate $ClNb(C_8H_8)_2$ formed in the initial stage of the process can be isolated by evaporating the mixture at this point to dryness, extracting the nonvolatile material with methylene chloride, optionally reducing the volume of the extract, and precipitating the product with ethyl ether. If $NbBr_5$ is used in place of $NbCl_5$, the corresponding $BrNb(C_8H_8)_2$ can be obtained in this manner.

Substitution of an equivalent amount of 4-biphenylyllithium for phenyllithium in essentially the process of the foregoing example will give $4-C_6H_5C_6H_4Nb(C_8H_8)_2$ as the product. If t-butyllithium is used, the product will be $t-C_4H_9Nb(C_8H_8)_2$. Use of m-tolyllithium will give $3-CH_3C_6H_4Nb(C_8H_8)_2$.

EXAMPLE 8

$CH_3Nb(C_8H_8)_2$

A. A mixture of 10.0 g of $NbCl_5$ and 200 ml of toluene was cooled to $-78°C$, and 165 ml of an 0.45 M solution of $K_2C_8H_8$ in tetrahydrofuran was added dropwise with stirring over a period of 1 hour. The mixture was warmed to room temperature, stirred for 30 minutes, and cooled again to $-78°C$, and 17 ml of a 2.2 M solution of $CH_3Li$ in ethyl ether was added dropwise with stirring over a period of 30 minutes. The mixture was warmed to room temperature and centrifuged, and the solid was homogenized in a blender in 250 ml of tetrahydrofuran. This mixture was also centrifuged; the supernatant liquids were combined, and the solution was reduced in volume under reduced pressure, with periodic filtration as solid precipitated, to give a total of 6.7 g of product (3 crops). The combined solids were stirred with 75 ml of acetonitrile, along with about 1 g of $ClNb(C_8H_8)_2$, which was inadvertently included. The mixture was filtered and the solid on the filter was dried under reduced pressure; yield 5.0 g.

A $^1H$ nmr of the crude product showed it to contain ca. 50% $CH_3Nb(C_8H_8)_2$ ($CD_2Cl_2$, $\tau$, 25°C): 4.14 (8, br s, $C_8H_8$), 4.65 (8, br s, $C_8H_8'$), 9.83 (3, br s, $CH_3$) with half-height widths of 2.4, 1.8 and 2.7 Hz, respectively. At 0°C, the half-height widths are 1.3, 1.0 and 1.7 Hz, respectively.

The crude product was extracted with 100 ml benzene and the resulting filtrate was taken to dryness in vacuo. The residue was dissolved in tetrahydrofuran and filtered. Addition of hexane gave approximately 0.100 g of red-brown crystals upon cooling at $-30°C$ for several hours. A $^1H$ nmr showed this product to be pure $CH_3Nb(C_8H_8)_2$.

In later experiments, a higher proportion of the desired compound in the crude product was realized by using about a 10% excess of $CH_3Li$.

B. The following procedure is the preferred method of making $CH_3Nb(C_8H_8)_2$. $(CH_3)_2NbCl_3$ was made by the method of Fowles et al., J. Chem. Soc. Dalton 1972, 2313. A solution of 8.52 g of this compound and 9.50 g of $NbCl_5$ in 500 ml of toluene was stirred for 3 hours. The solution of $CH_3NbCl_4$ thus prepared was cooled to $-78°C$, and 300 ml of an 0.47 M solution of $K_2C_8H_8$ in tetrahydrofuran was added dropwise with stirring over 45 minutes. The mixture was warmed to room temperature, allowed to stand overnight and centrifuged to separate the potassium chloride. The supernatant liquid was reduced in volume under reduced pressure, with periodic filtration as solid precipitated, to give 8.6 g of crystalline bis(cyclooctatetraene)methylniobium, identified by its $^1H$ nmr absorption spectrum. The product, together with the products of two other runs (total 12.5 g) was mixed with 350 ml of tetrahydrofuran; the mixture was stirred at 60°C and filtered, and the filtrate was allowed to stand overnight at $-30°C$. The plate-like crystals that precipitated were separated by filtration and dried; recovery, 4.6 g.

| Anal. calcd. for | | | |
|---|---|---|---|
| $C_{17}H_{19}Nb$: | C, 64.56; | H, 6.05; | Nb, 29.38 |
| Found: | C, 60.49; | H, 5.99; | Nb, 33.43 |
| | 60.13 | 5.78 | |
| | 60.18 | 5.78 | |

If an equivalent amount of octyllithium is substituted for methyllithium in essentially the procedure described in Part A, the product will be $C_8H_{17}Nb(C_8H_8)_2$. If dineopentylniobium trichloride is substituted for dimethylniobium trichloride in essentially the procedure of Part B, the product $(CH_3)_3 CCH_2Nb(C_8H_8)_2$ will be formed.

EXAMPLE 9

$C_6H_5Ta(C_8H_8)_2$

By essentially the method of Example 7, except that $TaCl_5$ was used in place of $NbCl_5$, 32.5 g of $TaCl_5$ in 400 ml of toluene, 400 ml of 0.46 M $K_2C_8H_8$ in tetrahydrofuran, and 50 ml of 17.82% $C_6H_5Li$ in benzene/ethyl ether were processed together. After centrifuging to remove potassium chloride, the filtrate was reduced to about 300 ml, allowed to stand for 3 days, and filtered. The filtrate was evaporated, and the residue was kept under a high vacuum overnight. The residue was dissolved in about 100 ml of tetrahydrofuran and allowed to stand overnight at $-25°C$, after which the solid that then precipitated was filtered and dried to give 3.0 g of brown crystals. Part of this product (2.0 g) was purified by washing with 20 ml of acetonitrile, washing with ethyl ether, drying (yield at this point 0.7 g), dissolving in 20 ml of tetrahydrofuran, filtering, allowing the filtrate to stand at $-30°C$ for 6 hours, and filtering again, to give 0.25 g of bis(cyclooctatetraene)-phenyltantalum, whose $^1H$ nmr absorption spectrum was virtually identical with that of $C_6H_5Nb(C_8H_8)_2$.

| Anal. calcd. for $C_{22}H_{21}Ta$: | C, 56.66; | H, 4.54 |
|---|---|---|
| Found: | C, 51.97; | H, 4.52 |
| | 51.80 | 4.35 |

The low carbon values are believed to be due to slight decomposition of the sample because of its extreme reactivity toward oxygen.

Substitution of an equivalent amount of 1-naphthyllithium for phenyllithium in the foregoing process will give $1-C_{10}H_7Ta(C_8H_8)_2$ as the product.

EXAMPLE 10

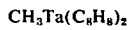

$(CH_3)_3TaCl_2$ was prepared by the method of Juvinall, J. Am. Chem. Soc., 86, 4202 (1964). A mixture of 5.0 g of this compound, 12.1 g of $TaCl_5$, and 250 ml of toluene was stirred overnight and filtered to remove traces of solid. The solution of $CH_3TaCl_4$ thus prepared was cooled to −78°C, 213 ml of 0.47 M $K_2C_8H_8$ in tetrahydrofuran was added over 1 hour with stirring, the mixture was warmed to room temperature, potassium chloride was separated by centrifugation, and the volume of the supernatant liquid was reduced under reduced pressure to 150 ml. The red-brown crystals of bis(cyclooctatetraene)methyltantalum, $CH_3Ta(C_8H_8)_2$, that precipitated were separated by filtration, washed with toluene and with pentane, and dried under reduced pressure; yield, 8.0 g.

An $^1H$ nmr in $CD_2Cl_2$ (40°C) showed a broad peak of area 16 at ca. 4.4 τ and a sharp singlet of area 3 at 9.95 τ. At 0°C (100 MHz) three peaks at 4.09 (s, 8), 4.64 (s, 8) and 9.95 (s, 3) characterize $CH_3Ta(C_8H_8)_2$.

Most of the product (7.5 g) was recrystallized by stirring in 150 ml of methylene chloride, filtering, and reducing the volume of the filtrate to about 15 ml under reduced pressure, with periodic filtration of the crystals that precipitated; recovery, 5.0 g.

| Anal. calcd. for $C_{17}H_{19}Ta$: | C, 50.38; | H, 4.73 |
|---|---|---|
| Found: | C, 49.38; | H, 4.66 |
|  | 49.68 | 4.72 |
|  | 49.28 | 4.71 |

A solution of 4.0 g $(CH_3)_3TaCl_2$ in 100 ml of toluene was cooled to −78°C, and 32 ml of an 0.47 M solution of $K_2C_8H_8$ in tetrahydrofuran was added dropwise with stirring over 15 minutes. The mixture was warmed to room temperature, stirred for 30 minutes at room temperature, and centrifuged to remove potassium chloride. The liquid centrifugate was evaporated to a volume of about 100 ml under reduced pressure, allowed to stand 3 days at −30°C, and further reduced in volume to about 20 ml. The greenish crystals of cyclooctatetraenetrimethyltantalum that precipitated were separated by filtration and dried; yield 2.9 g. A sample of the product was sublimed at 100°C/0.001 mm to give a pyrophoric blue sublimate. $^1H$ nmr $(C_6D_6,τ)$: 4.03 (8, s, $C_8H_8$), 9.17 (9, s, methyl).

Another sample of the product was recrystallized from toluene to give blue crystals that were soluble in benzene to give a turqoise-blue solution. Mass-spectral analysis of the recrystallized product showed a parent ion of mass 330.0810 (calcd. 330.0787).

Another sample of the product, prepared essentially as described above and crystallized from toluene, was analyzed.

| Anal. calcd. for | | | |
|---|---|---|---|
| $C_{11}H_{17}Ta$: | C, 40.01; | H, 5.19; | Ta, 54.80 |
| Found: | C, 39.51; | H, 5.30; | Ta, 52.18 |
|  | 39.59 | 5.26 |  |
|  | 39.83 | 5.23 |  |

The products of the invention, because of their sensitivity to oxygen, are useful for removing small amounts of oxygen from gases and mixtures of gases.

As illustrated in the following examples, the products of the invention are also useful as catalysts in the oligomerization of ethylene.

EXAMPLE A

A solution of 2.0 g of $C_6H_5Nb(C_8H_8)_2$ in 50 ml of tetrahydrofuran was charged to a 100 ml stainless-steel shaker tube. The tube was cooled, evacuated, pressured with ethylene, and heated at 90°C and 50 atmospheres for 4 hours, with repressuring with ethylene as required. It was cooled to room temperature, and volatile materials were allowed to escape into and through a trap cooled with liquid nitrogen. The liquid in the trap was warmed to −78°C and bled to the atmosphere. The material that remained liquid at −78°C was allowed to warm to room temperature, where it became a gas. Analysis of this gas by gas chromatography and mass spectrometry showed it to contain 72.1% 1-butene.

The liquid remaining in the shaker tube was filtered and evaporated under high vacuum, and the evaporated material was trapped at liquid-nitrogen temperature. Analysis of the trapped material, again by gas chromatography and mass spectrometry, showed the presence of the following materials in decreasing amounts: 1- or 2-butene, $C_6H_{12}$, $C_6H_{12}$ isomer, $C_{10}H_{18}$, $C_{10}H_{20}$, $C_{12}H_{16}$, $C_8H_{14}$, and $C_8H_{16}$.

EXAMPLE B $(CH_3)_3TaC_8H_8$ was tested as a catalyst for ethylene oligomerization by essentially the method of Example A, except that benzene was used as the solvent in place of tetrahydrofuran. Analysis of the volatile products showed the presence of an appreciable amount of mixed butenes.

I claim:

1. A cyclooctatetraene complex having the formula: $Q^+M(C_8H_8)_3^-$, $RM(C_8H_8)_2$, or $(CH_3)_3Ta(C_8H_8)$, wherein M is tantalum or niobium,
R is Cl, Br, alkyl of 1 to 8 carbons or aryl of 6 to 12 carbons,
$Q^+$ is one equivalent of an alkali metal ion, an alkaline earth metal ion, $R'R''_3N^+$, $R''_4P^+$, or $R''_4As^+$, wherein R' is alkyl of 1 to 8 carbons and R'' is alkyl of 1 to 8 carbons or aryl of 6 to 12 carbons.

2. A cyclooctatetraene complex of claim 1 having the formula $Q^+M(C_8H_8)_3^-$.

3. A cyclooctatetraene complex of claim 2 wherein M is niobium.

4. A cyclooctatetraene complex of claim 3 wherein $Q^+$ is $K^+$.

5. A cyclooctatetraene complex of claim 3 wherein $Q^+$ is $(C_6H_5)_4As^+$.

6. A cyclooctatetraene complex of claim 3 wherein $Q^+$ is $Li^+$.

7. A cyclooctatetraene complex of claim 2 wherein M is tantalum.

8. A cyclooctatetraene complex of claim 7 wherein $Q^+$ is $K^+$.

9. A cyclooctatetraene complex of claim 7 wherein $Q^+$ is $(C_6H_5)_4As^+$.

10. A cyclooctatetraene complex of claim 7 wherein $Q^+$ is $Li^+$.

11. A cyclooctatetraene complex of claim 1 having the formula
$RM(C_8H_8)_2$.

12. A cyclooctatetraene complex of claim 11 wherein M is niobium.

13. A cyclooctatetraene complex of claim 12 wherein R is methyl.

14. A cyclooctatetraene complex of claim 12 wherein R is phenyl.

15. A cyclooctatetraene complex of claim 11 wherein M is tantalum.

16. A cyclooctatetraene complex of claim 15 wherein R is methyl.

17. A cyclooctatetraene complex of claim 15 wherein R is phenyl.

18. A cyclooctatetraene complex of claim 1 having the formula $(CH_3)_3Ta(C_8H_8)$.

* * * * *